United States Patent [19]
Rutzen et al.
[11] 4,281,196
[45] Jul. 28, 1981

[54] QUATERNARY AMMONIUM COMPOUNDS, THEIR PREPARATION, AND THEIR USE AS SOFTENING AGENTS

[75] Inventors: Horst Rutzen, Langenfeld; Jochen Heidrich, Düsseldorf; Martin Bischoff, Gelsenkirchen; Udo Kloubert, Erkrath; Peter Waltenberger, Hilden; Ingo Wegener, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 83,850

[22] Filed: Oct. 11, 1979

[30] Foreign Application Priority Data

Oct. 12, 1978 [DE] Fed. Rep. of Germany ....... 2844451
Oct. 12, 1978 [DE] Fed. Rep. of Germany ....... 2844463

[51] Int. Cl.³ .............................................. C07C 91/26
[52] U.S. Cl. .................................... 564/292; 564/505; 564/475; 564/294; 252/8.9; 260/459 R; 260/1
[58] Field of Search .................... 260/567.6 M, 584 B, 260/459 R; 424/329; 252/8.75; 564/292, 294

[56] References Cited

U.S. PATENT DOCUMENTS

| | | | |
|---|---|---|---|
| 3,141,905 | 7/1964 | Longley | 260/567.6 M |
| 3,445,440 | 5/1969 | Susi et al. | 260/567.6 M |
| 3,454,646 | 7/1969 | Patton et al. | 260/584 B |
| 3,891,709 | 6/1975 | Higuchi et al. | 260/584 B |
| 3,972,855 | 8/1976 | Martinsson et al. | 260/567.6 M |
| 4,009,255 | 2/1977 | Kalopissis et al. | 260/567.6 M |
| 4,074,970 | 2/1978 | Feigin | 260/567.6 M |
| 4,093,663 | 6/1978 | Harris | 260/567.6 M |
| 4,134,970 | 1/1979 | Panke et al. | 260/567.6 M |

*Primary Examiner*—Robert Gerstl
*Assistant Examiner*—James H. Reamer
*Attorney, Agent, or Firm*—Hammond & Littell, Weissenberger and Muserlian

[57] ABSTRACT

This invention is directed to quaternary compounds of the formula

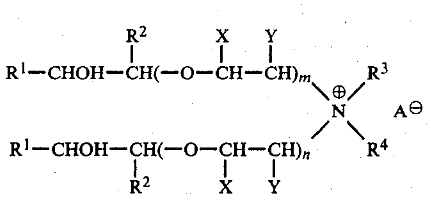

(I)

wherein $R^1$ represents an aliphatic hydrocarbon radical of from about 1 to 21 carbon atoms; $R^2$ represents hydrogen or has the same meaning as $R^1$, the total number of carbon atoms in $R^1$ and $R^2$ being from 6 to 22, and, when $R^2$ is hydrogen, $R^1$ has from 6 to 21 carbon atoms; $R^3$ represents an alkyl or hydroxyalkyl group having from 1 to 4 carbon atoms or a radical of formula

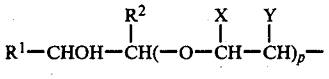

(Ia)

wherein R and R are devined above, X and Y are each either hydrogen or a methyl group, with the proviso that X and Y cannot both be a methyl group, and p is an integer of from 1 to 20; $R^4$ represents an alkyl radical of from 1 to 4 carbon atoms; m and n are integers of from about 1 to 20; and A⊖ is an anion. The quaternary compounds are useful as fabric softeners.

13 Claims, No Drawings

QUATERNARY AMMONIUM COMPOUNDS, THEIR PREPARATION, AND THEIR USE AS SOFTENING AGENTS

FIELD OF THE INVENTION

This invention is directed to novel quaternary compounds. More specifically, this invention is directed to novel quaternary compounds having two or three long-chained hydroxyalkoxyalkyl radicals, a process for their preparation, and their use as a fabric softener in the treatment of textiles.

BACKGROUND OF THE INVENTION

During the manufacturing of textiles and during washing textiles, as a result, a certain brittling of the materials sets in in most textiles. To eliminate this inconvenience, treating methods are employed to restore softness and suppleness to the textiles or to redefine the character of the material according to fashion viewpoints. In addition, technical requirements such as antistatics, wrinkle recovery, yellowing, surface smoothness, and the like, are considered in determining further treatment of the textiles.

It is known that quaternary tetraalkyl-ammonium compounds with two long-chained, generally $C_{16}$–$C_{18}$ alkyl radicals are suitable as softening agents. These textile softeners are used widely, on the one hand, in the manufacture of textiles and, on the other hand, in the treatment of textiles both in commercial laundries and in households. It is assumed that these cationic quaternary ammonium compounds are easily absorbed on the textile substrate because of their positive charge.

The most frequently used textile softener of this compound class is ditallow-alkyl- or distearyldimethyl ammonium chloride. This textile softener has excellent softening properties, as well as tinctorial power and substantivity, and can be used under all normal conditions both in the finishing and in the care of textiles. However, it also has drawbacks. For example, the commonly used cationic softeners yellow at the drying and/or condensation or thermofixing temperatures used in the textile industry, a property which is not acceptable in white goods or pastel-colored articles. Another drawback of the cationic softeners is that the textiles finished with them become hydrophobic, which is particularly undesirable with regard to cellulose fibers, which are especially used for their excellent absorption power in sanitary articles, such as cotton, diapers, sanitary napkins, or tampons, or in terry- and tricot materials.

In treating synthetic fibers, the antistatic effect of such textile softeners becomes apparent, in addition to the softening property or the softening treatment. However, the softening treatments representing the state of the art have only a modest effect. The textiles treated with these substances show reduced absorbency, as compared to untreated fabrics, which results in unpleasant feel to the user in, for example, garments worn in contact with the skin and Turkish towels. Frequently these textile softeners can not be completely removed from the fabric by washing, so that even when the softening substances are used in proper dosage, they sometimes accumulate. This likewise results in a reduced absorbency of the textiles.

Another serious drawback of these textile softeners is their relatively high production cost, since it is necessary to start from secondary fatty amines which are obtained primarily from natural fatty acids or fatty alcohols of frequently varying quality.

There has been no lack of attempts to eliminate these drawbacks. Thus, it is known from U.S. Pat. No. 3,636,114 that absorbency can be improved by using quaternary ammonium compounds with two long-chained 2-hydroxyalkyl radicals. German Published Application (DOS) No. 22 56 234 discloses quaternary ammonium compounds with two long-chained 2-hydroxy-3-alkoxypropyl groups. The softeners known from German Published Application (DAS) No. 16 19 043 contain quaternary ammonium compounds with only one long alkyl radical and three short alkyl radicals, where the three short alkyl radicals can contain hydroxyl or ether groups. Dutch Patent Application N. 68/08958 and U.S. Pat. No. 3,591,405 describe ammonium compounds whose hydrophobic radicals represent hydroxyalkyl-groups or alkyl groups linked with the nitrogen by ethoxy groups. However, these solutions were not satisfactory, either because the modified quaternary ammonium compounds were difficult to produce, and thus unsuitable for use in practice, or because the softening action was too weak.

Applicants have surprisingly found that useful quaternary compounds can be prepared in a relatively straightforward manner from readily available, inexpensive raw materials. These compounds, which impart absorbency and good softening properties during the processing or washing of treated textiles, can be removed completely when the textiles are washed.

OBJECTS OF THE INVENTION

It is an object of this invention to provide novel quaternary ammonium compounds useful as softening agents.

It is also an object of this invention to provide novel tertiary amines useful in preparing the quaternary ammonium compounds.

It is further an object of this invention to provide methods of preparing the quaternary ammonium compounds and of using them as softening agents.

These and other objects of the invention will become more apparent in the discussion below.

DESCRIPTION OF THE INVENTION

This application is directed to novel quaternary ammonium compounds of the formula

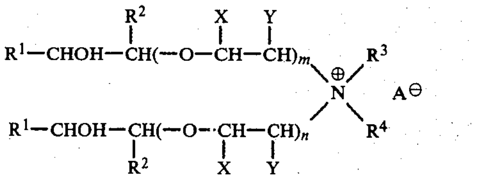

(I)

wherein $R^1$ represents an aliphatic hydrocarbon radical of from about 1 to 21 carbon atoms; $R^2$ represents hydrogen or has the same meaning as $R^1$, the total number of carbon atoms in $R^1$ and $R^2$ being from 6 to 21 carbon atoms; $R^3$ represents an alkyl or hydroxyalkyl group having from 1 to 4 carbon atoms or a radical of formula

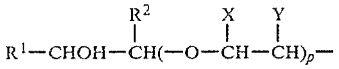

(Ia)

wherein $R^1$ and $R^2$ are as defined above, X and Y are each hydrogen or a methyl group, with the proviso that X and Y cannot both be a methyl group, and p is an integer of from 1 to 20; $R^4$ represents an alkyl radical of from 1 to 4 carbon atoms; m and n are integers of from about 1 to 20; and $A^\ominus$ is an anion. The compounds of Formula I are readily prepared and have excellent wash-improving properties.

Preferably, with regard to the compounds of Formula I, $R^1$ represents an alkyl group of from about 1 to 21 carbon atoms, $R^2$ is hydrogen, $R^3$ represents an alkyl group having from 1 to 4 carbon atoms or a hydroxyalkyl group bearing from 2 to 4 carbon atoms, X and Y each represent hydrogen, and m, n, and p each represent a number of from 1 to 3. In another preferred embodiment, $R^3$ represents the radical of Formula Ia and/or m, n, and p each represent 1.

The anion $A^\ominus$ represents an anion split off, or separated, from the quaternizing agent, such as, e.g., a chloride or a methyl sulfate ion. The anion $A^\ominus$ can also be another anion commonly used in quaternary ammonium compounds, such as, e.g., a bromide or ethyl sulfate ion.

Compounds of Formula I with 2 or 3 long-chain radicals, in which $R^1$ denotes an alkyl radical with, preferably, from about 8 to 18 carbon atoms and $R^2$ represents hydrogen, are particularly suitable as textile softeners because of their balanced properties in use. Depending on the desired degree of hydrophilic properties, the compounds can contain from about 1 to 20 ethoxy or propoxy groups in each long radical product, long radicals containing from 1 to 3 ethoxy groups, especially 1 ethoxy group, being particularly preferred. Compounds of Formula I include, for example, the following:

Bis(5-hydroxy-3-oxa-pentadecyl)-dimethyl-ammonium-methylsulfate
Bis(5-hydroxy-3-oxa-heptadecyl)-dimethyl-ammonium-methylsulfate
Bis(5-hydroxy-3-oxa-$C_{15/17}$-alkyl)-dimethyl-ammoniummethylsulfate
Bis(5-hydroxy-3-oxa-$C_{19/21}$-alkyl)-dimethyl-ammoniummethylsulfate
Bis(5-hydroxy-3-oxa-$C_{15/17}$-alkyl)-methyl-2-hydroxyethylammoniummethylsulfate
Bis(5-hydroxy-3-oxa-undecyl)-dimethyl-ammonium-chloride
Bis(5-hydroxy-3-oxa-4-hexyl-tridecyl)-2-hydroxyethyl-methylammoniumchloride
Bis(5-hydroxy-3-oxa-4-octyl-nonadecyl)-dimethyl-ammoniumchloride
Bis(5-hydroxy-3-oxa-2-methyl-heptadecyl)-dimethyl-ammoniumchloride
Bis(11-hydroxy-3,6,9-trioxa-tricosyl)-dimethyl-ammoniumchloride
Tris(5-hydroxy-3-oxa-pentadecyl)-methyl-ammonium-chloride
Tris(5-hydroxy-3-oxa-pentadecyl)-methyl-ammonium-methylsulfate
Tris(5-hydroxy-3-oxa-$C_{15/17}$-alkyl)-methyl-ammonium-chloride
Tris(5-hydroxy-3-oxa-heptadecyl)-methyl-ammonium-methylsulfate
Tris(5-hydroxy-3-oxa-$C_{19/21}$-alkyl)-methyl-ammonium-chloride
Tris(5-hydroxy-3-oxa-undecyl)-methyl-ammonium-chloride
Tris(5-hydroxy-3-oxa-undecyl)-2-hydroxyethyl-ammoniumchloride
Tris(5-hydroxy-3-oxa-4-octyl-heptadecyl)-ethyl-ammoniumchloride
Tris(5-hydroxy-3-oxa-4-pentadecyl-hexyl)-methyl-ammoniummethylsulfate
Tris(5-hydroxy-3-oxa-2-methyl-nonadecyl)-methyl-ammoniumchloride
Tris(14-hydroxy-tetrapropoxy-pentacosyl)-methyl-ammoniummethylsulfate The preparation of the compounds of Formula I is also an aspect of the invention. The compounds of Formula I are prepared in a simple manner and in high yield from tertiary amines of formula

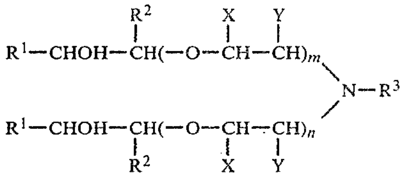

(II)

wherein $R^1$, $R^2$, $R^3$, X, Y, m, and n are as described above. The compounds of Formula II, and the preparation thereof, are similarly subjects of this invention.

The compounds of Formula II are prepared by reacting epoxyalkanes of the formula

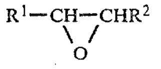

(III)

wherein $R^1$ and $R^2$ are as described above, with a polyalkanol amine of the formula

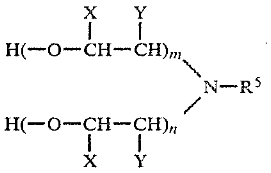

(IV)

wherein $R^5$ represents an alkyl radical of from 1 to 4 carbon atoms or a radical of the formula $H(—OCHX—CHY)_p—$ wherein X, Y, m, n, and p are as described above, in the presence of a catalyst under normal pressure and elevated temperature. The resulting tertiary amine of Formula II is subsequently quaternized with an alkylating agent to introduce the $R^4$ group to form a quaternary ammonium compound of Formula I.

The epoxyalkanes of Formula III to be used as starting materials are inexpensive and are available in large quantities. The epoxyalkanes are obtained, or derived, in known manner from the corresponding olefins or olefin mixtures. The 1,2-epoxyalkanes are obtained from 1,2-monoolefins, which are prepared by, for example, polymerization of ethylene with organic aluminum compounds as catalysts, or by thermal cracking of paraffin-hydrocarbons. Examples of preferred epoxyalkanes are the compounds 1,2-epoxy-dodecane, 1,2-epoxy-tetradecane, 1,2-epoxy-hexadecane, 1,2-epoxy-octadecane, and epoxide mixtures, such as $C_{12/14}$-1,2-epoxide with about 70% by weight $C_{12}$ epoxyalkane and about 30% by weight $C_{14}$ epoxyalkane, or $C_{16/18}$-1,2-epoxide with about 40% by weight $C_{16}$ epoxyalkane and about 60% by weight $C_{18}$ epoxyalkane.

The epoxyalkanes having interior (e.g., 3,4) epoxide groups are obtained, for example, be epoxidizing olefins or olefin mixtures which are obtained by catalytic dehydration or by chlorination/dehydration of linear paraffin hydrocarbons. Monoolefins with an interior double bond can also be prepared by isomerization of alphaolefins. Preferred interior epoxyalkanes of a $C_{11/14}$-olefin fraction contain about 22% by weight of $C_{11}$ epoxyalkane, about 30% by weight of $C_{12}$ epoxyalkane, about 26% by weight of $C_{13}$ epoxyalkane, and about 22% by weight of $C_{14}$ epoxyalkane. A likewise preferred epoxyalkane mixture of a $C_{15/18}$-olefin fraction contains about 26% by weight of $C_{15}$ epoxyalkane, about 35% by weight of $C_{16}$ epoxyalkane, about 32% by weight of $C_{17}$ epoxyalkane, and about 7% by weight of $C_{18}$ epoxyalkane.

Preferred di- or trialkanolamines are, e.g., N-methyldiethanolamine or triethanolamine. By use of alkoxylated alkanolamine, the hydrophilic group of the end products can be varied within certain limits and be adapted to desired use. Sodium alcoholates, especially sodium methylate, are suitable as catalysts for the reaction of epoxyalkanes of Formula III with polyalkanolamines of Formula IV. The catalysts are preferably used in amounts of from about 0.1–1.0% by weight, based on the weight of the entire reaction batch.

The reaction of the epoxyalkane with the alkanolamine takes place in high yield without the formation of by-products. The further reaction to compounds of Formula II is preferably carried out with a ratio of epoxyalkane to alkanolamine such that one alkanol equivalent is used per mol of epoxyalkane, that is, one mol epoxyalkane is reacted with one-half mol dialkanolamine or one-third mol trialkanolamine. With excess alkanolamine or with an incomplete reaction, resulting from shortened reaction time, mixtures of compounds with $R^3$ in Formula II being alkyl, on the one hand, and hydroxyalkyl, on the other hand, are obtained. These technical mixtures likewise have, after quaternization, the desired textile-softening properties while maintaining the absorbency of the softened textiles. Any unreacted starting products are distilled off from the reaction product, preferably at low pressure and low temperatures to prevent darkening of the reaction products.

Suitable alkylating agents include, e.g., methylchloride, methyl bromide, dimethyl sulfate, diethyl sulfate, dimethyl sulfate, and, particularly, methyl chloride. In quaternization with methyl chloride as an alkylating agent, it is advisable to work under a pressure of up to about 10 bar, preferably of from about 3 to 6 bar, and at a temperature preferably of from about 80° to 120° C., optionally, in the presence of solvents, such as isopropyl sulfate and/or water. Quaternization with dimethylsulfate as an alkylating agent can be effected at normal pressure and at temperatures of from about 50° to 100° C., preferably of from 60° to 80° C.

Quaternization is also possible by reacting the amines with a low epoxide and subsequent acid treatment for the introduction of the anion.

The new products can be easily dispersed in water and in mixtures of water and low alcohols to stable dispersions. Textiles treated with these products in a textile finishing or washing process have a soft velvety feel with good absorbency and good wettability.

The compounds of Formula I used as textile softeners can be readily mixed with other textile softeners, antimicrobics, optical brighteners, nonionic and cationic surface-active agents and other customary components of textile treating agents, if desired, particularly for liquid preparations. The use of the new quaternary ammonium compounds as textile softeners, particularly in liquid preparations for the after-treatment of fabrics in the rinsing bath of the washing process, in hand- or machine-washing, or in the drier where the preparations contain from about 1 to 40% by weight of the compounds of Formula I and at least one diluent, as well as, optionally, other customary additives, for liquid after-treatment agents, is therefore another aspect of the invention.

The textile softeners according to the invention can be used in various ways in laundries and in households for the after-treatment of washed fabrics, depending on the selection of the drying method. If the laundry is dried in a drier, it can be sprayed directly with a dispersion of the active substance. Also, the active substance can be brought into contact with the laundry by use of a carrier, i.e., indirectly. For example, a dispersion or preparation of the active substance can be sprayed onto the inner walls of the drier before the drier is loaded with laundry, or a large-surfaced carrier saturated with the liquid dispersion or preparation can be added to the laundry, whereby the textile softener is absorbed on the fabric during the drying process. When the laundry is dried by hanging, the softener is used primarily in the last rinsing bath of the hand- or machine-washing process, particularly, the machine-washing process. The amounts of the preparation dissolved in the rinsing liquor are such that the concentration of the active substance of Formula I is from about 0.05–1.5, preferably from about 0.1–1.0, grams per liter of liquor.

Water and/or water-soluble organic solvents can be used as a diluent for liquid textile softeners. Suitable water-soluble organic solvents are the lower alcohols with from about 1 to 5 carbon atoms, such as methanol, ethanol, propanol, isopropyl alcohol, n-butanol, isobutanol, and amyl alcohol; the lower ketones acetone and methylethyl ketone; as well as ethylene glycol, propylene glycol, diethylene glycol, and their mono- or diether derivatives, particularly with methyl and ethyl radicals.

The active ingredients of the compounds of Formula I are also suitable for the manufacture of pourable textile finishing agents in powder form. Suitable diluents for such powdery compositions include, for example, urea, acetamide, and sodium sulfate. Optionally, other customary components for such finishing agents can be present provided they are present in solid form.

Other common components of textile softeners are, for example, dispergators, i.e., peptizing agents, optical brighteners, antimicrobial substances, acid additives, solubilizers, dyes, and perfumes.

The compounds of Formula I can also be used together with known textile softeners of the type of the quaternary ammonium compounds, such as di-tallowalkyl dimethylammonium chloride, or with known textile softeners with an amide structure of the condensation products of fatty acids with hydroxyalkyl polyamines, e.g., the condensation product of 1 mol tallow and 1 mol 2-hydroxyethylethylene-diamine. The addition of known antimicrobial substances of the type of the antimicrobial quaternary ammonium compounds which are suitable for use in textile softeners, such as benzyl dodecyl dimethylammonium chloride, as well as antimicrobial nitroalcohols, or phenol derivatives or carbamates thereof, and the like is also possible.

The liquid after-treatment preparations of particular practical interest, where the new substances of Formula I can be used, generally have the following composition, based on the total weight of the preparation:

from about 2.0 to 30.0, preferably from about 5.0 to 25.0, % by weight of active substance of Formula I;
from about 0.2 to 6.0, preferably from about 0.5 to 3.0, % by weight of dispergators;
from about 0.0 to 30.0, preferably from about 1.0 to 15.0, % by weight of water-soluble organic solvents;
from about 0.0 to 10.0, preferably from about 0.3 to 7.5, % by weight of other customary components of after-treatment agents; and
balance water.

At least one of the following components can be present in the indicated amount, based on the weight of the total preparation, as one of the customary components in after-treatment preparations:

from about 0.2 to 5.0% by weight of other textile softeners which are different from the compound according to Formula I;
from about 0.2 to 3.0% by weight of antimicrobial substances;
from about 0.2 to 6.0% by weight of acid additive;
from about 0.01 to 0.5% by weight of cotton optical brightener;
from about 0.01 to 0.5% by weight of polyamide optical brightener;
from about 0.01 to 0.5% by weight of perfume; and
from about 0.00001 to 0.05% by weight of dye.

Described below with greater particularity are the components contained in the textile softeners, in addition to the compound according to Formula I.

Particularly suitable as dispergators, which can be contained in liquid or powdered textile softeners, are the nonionic surface active agents ("nonionics"). These include products which owe their hydrophilic properties to the presence of polyether chains, aminoxide, sulfoxide or phosphinoxide groups, alkylolamide groups, as well as, generally, to an abundance of hydroxyl groups. These nonionics contain in the molecule at least one hydrophobic radical of from 8 to 26, preferably from 10 to 20, and more preferably from 12 to 18, carbon atoms, and at least one nonionic, water-solubilizing group. The hydrophobic radical, preferably saturated, is mostly of an aliphatic, in some cases of an alicyclic, nature. It can be linked to the water-solubilizing group directly or through intermediate members. Intermediate members can be, for example, benzene rings, carboxylic ester or carbonamide groups, ether- or ester-type radicals of polyvalent alcohols, such as those of ethylene alcohol, propylene alcohol, glycerin or of corresponding polyether radicals.

Of particular practical interest are products which are obtained by the addition of ethylene oxide and/or glycide on fatty alcohols, alkyl phenols, fatty acids, fatty amines, fatty acid- or sulfonic acid amides, these nonionics containing in the molecule from about 4 to 100, preferably from about 6 to 40, and particularly from about 8 to 20, ether radicals, especially ethylene glycolether radicals. In addition, propylene or butylene glycolether radicals or propylene or butylene polyether chains can be present in these polyether chains or at their ends.

The nonionics also comprise products which are obtained by ethoxylation until they become water-soluble, of water-insoluble polypropylene glycols, of water-insoluble propoxylated lower aliphatic alcohols containing from 1 to 8, preferably from 3 to 6 carbon atoms, or from water-insoluble, propoxylated alkane diamines.

The nonionics also comprise fatty acid or sulfonic acid alkylolamines which are derived, for example, from mono- or diethanolamine, from dihydroxypropylamine, or from other polyhydroxyalkylamines, e.g., from the glycamines. They can be replaced by amides from higher primary or secondary alkylamines and polyhydroxycarboxylic acids.

The capillary active aminoxides include, e.g., the products derived from higher tertiary amines with one hydrophobic alkyl radical and two shorter alkyl- and/or alkylol radicals, each containing up to 4 carbon atoms.

In addition to the useful water-soluble surface-active agents, or tenside, water-soluble or water-emulsifiable or dispersible comounds which are suitable as nonionic dispergators are those which either contain no hydrophobic radicals, in the sense of the above-described nonionic surfactants, or where the nature or the number of the hydrophilic groups is not sufficient to obtain complete water-solubility. The first group includes, e.g., solid or liquid polyethylene glycols, which can be considered condensation polymers of ethylene oxide with ethylene glycol or water, ethylene-oxide adducts of glycerin or other polyalcohols, and the like. The second group includes, e.g., partial fatty acid glycerides, or alkoxylation products which are partially or wholly water-insoluble, e.g., those with from 2 to 5 ethylene glycol ether radicals in the molecule.

Acid additives include inorganic and non surface-active organic acids with from 2 to 8 carbon atoms, e.g., amidosulfonic acid, urea compounds of orthophosphoric acid, boric acid, oxalic acid, lactic acid, glycolic acid, citric acid, tartaric acid, benzoic acid, phthalic acid, gluconic acid, acetic acid, and propionic acid, as well as the benzene, toluene and xylene sulfonic acids, sulfoacetic acid, or sulfobenzoic acid, or acid alkali salts of these acids. Glycolic acid and citric acid are preferred because of their ready availability and nontoxicity.

The antimicrobial substances encompass bactericidal or bacteriostatic, or fungicidal or fungistatic compounds. These substances should be either water-soluble themselves or in the form of their salts. Antimicrobial quaternary ammonium compounds which are suitable as additives are particularly those which contain in the molecule, in addition to one long-chained aliphatic and two short-chained aliphatic hydrocarbon radicals, an aromatic radical linked by an aliphatic carbon atom to the nitrogen atoms, or an organic radical containing aliphatic double bonds. Examples of such antimicrobial quaternary ammonium compounds are the following: dimethyl-benzyl-dodecylammonium chloride, dimethyl-benzyl-tetradecylammonium chloride, dimethyl-(ethylbenzyl)-dodecyl-ammonium chloride, dimethyl-benzyl-decylammonium bromide, diethyl-benzyl-dodecylammonium chloride, diethyl-benzyl-octyl-ammonium chloride, dibutyl-allyl-, methyl-ethyl-benzyl-, ethyl-cyclohexyl-allyl- and ethyl-crotyl-diethylaminoethyl-dodecylammonium chloride.

Other suitable antimicrobial substances are the lower alcohols with from 3 to 5 carbon atoms substituted by both bromine and a nitro group, e.g., 2-bromo-2-nitropropane-1,3-diol, 1-bromo-1-nitro-3,3,3-trichloro-2-propanol, and 2-bromo-2-nitro-butanol.

Also suitable as antimicrobial substances are phenol compounds such as the halogenated phenols having from 1 to 5 halogen substituents, particularly chlorinated phenols; alkyl-, cycloalkyl-, aralkyl-, and phenylphenols with from 1 to 12 carbon atoms in the alkyl radical and with from 1 to 4 halogen substituents, particularly chlorine and bromine, in the molecule; alkyl bisphenols, particularly derivatives substituted by from 2 to 6 halogen atoms and lower alkyl- or trifluormethyl groups, optionally, with an alkylene bridge member consisting of from 1 to 10 carbon atoms; hydroxybenzoic acids or their esters and amides, particularly anilides, which can be substituted in the benzoic acid- and/or aniline moiety, particularly by 2 or 3 halogen atoms and/or trifluoromethyl groups; and o-phenoxyphenols which can be substituted by from 1 to 7, preferably from 2 to 5, halogen atoms and/or hydroxy, cyano, carbomethoxy, or carboxyl groups or a lower alkyl. An especially preferred derivative of o-phenoxyphenol is the 2-hydroxy-2',4,4'-trichlorodiphenyl ether.

In a broader sense, antimicrobial substances also include additives such as formaldehyde, sorbic acid, and sodium fluoride, which are used as preservatives in the preparations.

Another aspect of the invention is a method for using compounds of Formula I for treating textile material during the finishing process by impregnation by means of aqueous/alcoholic liquors of agents containing compounds of Formula I, optionally in combination with other softeners, wetting agents, dispergators, or other agents customarily used in the treating textiles.

The finishing of the textile materials during the processing stage is preferably effected by spraying, padding, dabbing, or extraction. The treatment normally takes place at temperatures between about 10° and 50° C., and it can also be effected directly in the dye bath, provided the dyes used are of a cationic nature. Useful textile materials include fabrics, knittings or fleeces, yarns, fibers, slubbings of naturally or regenerated cellulose fibers, wool, polyamide-, polyester- or polyacrylonitrile fibers, as well as mixtures of these fibers.

The amount to be used according to the invention depends on the form of application and should be in the dye on a padding machine in an amount of from 2 to 10 g/liter of dry substance, with squeezing effectiveness preferably between about 50 and 100%. In the extraction method, from about 0.1 to 0.6% by weight of the compounds of the invention, based on the weight of the material, is added in the form of an aqueous preparation. The treatment time is from about 10 to 30 minutes. The pH value of the finishing liquor should preferably be between about 3 and 7.5. The pH can be adjusted by the addition of inorganic or, preferably, lower organic carboxylic acids, such as formic or acetic acid.

In addition to a soft, supple feel, the treated textile materials demonstrate excellent hydrophilic properties, cellulose fiber materials having practically the same properties as untreated materials. Excellent antistatic effects are achieved in synthetic fiber materials. Even after the application of higher temperatures in the further processing of the treated textile materials, no yellowing is observed, in contrast to the known cationic treating agents.

The trating agents according to Formula I can be used during the finishing process together with other cationic and/or nonionic softening agents commonly used for softening textiles. These are particularly: fatty acid polyamides from 1 mol of a $C_8$–$C_{22}$-fatty acid and 1 mol of a polyalkylene polyamine or hydroxypolyalkylene polyamide, e.g., diethylene triamine, tetraethylene pentamine, or aminoethylethanolamine, as well as $C_8$–$C_{22}$-fatty alcohol polyglycol ethers, e.g., the adducts of from 2 to 20 mols of ethylene oxide with 1 mol of a $C_{12/18}$-fatty alcohol. This provides another possibility of controlling the hydrophilic texture, or feel influencing, and softening properties; however, a certain tendency to yellowing of the fatty acid polyaminamide must be taken into consideration. Such combinations have, for example, the following composition: (i) from about 30 to 90, preferably from about 40 to 60, % by weight of a compound of Formula I, with (ii) from about 10 to 70, preferably from about 40 to 60, % by weight of a fatty acid polyaminamide, of from about 10 to 70, preferably from about 40 to 60, % by weight of a fatty alcohol polyglycol ether, or from about 10 to 70, preferably from about 40 to 60, % by weight of a mixture of fatty acid polyaminamide and fatty alcohol polyglycol ether.

The addition of perfumes or preservatives may be advisable.

Both the preparations containing exclusively the compounds of Formula I and the above-mentioned combination products are produced and distributed preferably as aqueous or aqueous/alcoholic concentrates with from about 5 to 30% by weight, preferably from about 10 to 25% by weight, of solid substance. Suitable solvents are lower alcohols or glycols having from 2 to 6 carbon atoms, such as ethanol, isopropanol, or ethyl glycol monobutyl ether. However, the products can also be produced and used in anhydrous or solvent-free form.

EXAMPLES

The following examples are intended to illustrate the invention and are not to be construed as limiting the invention thereto.

EXAMPLE 1

Preparation of tris(5-hydroxy-3-oxa-$C_{15/17}$-alkyl)-methylammonium chloride An amount of 1194 g (6 mols) of 1,2-epoxyalkane with about 70% by weight $C_{12}$ and about 30% by weight of $C_{14}$ was added to 298.4 g (2 mols) of triethanolamine and 6 g of 30% by weight methanolic sodium methylate solution at 180° C. under a nitrogen atmosphere and under stirring within 30 minutes, and the admixture was then stirred for another hour. Next, 80 g of first runnings were distilled off at 0.8 mbar and a sump temperature of 240° C. Tris(5-hydroxy-3-oxa-$C_{15/17}$-alkyl)-amine, with an amine number of 84.4 and in an amount of 1407 g, remained as residue in the distillation flask. One mol, 664.7 g, of this product was introduced into an evacuated 2 liter autoclave together with 95.4 g of water and 143 g of isopropyl alcohol. Methyl chloride at 5 bar was introduced at 100° C. After 4.25 hours the quaternization was practically complete (quaternary portion—93.5% by weight, amine number of a sample—2.3). After cooling to room temperature and pressure equalization, a 75% solution of tris(5-hydroxy-3-oxa-$C_{15/17}$-alkyl)-methylammonium chloride was obtained.

EXAMPLE 2

Preparation of bis(5-hydroxy-3-oxa-$C_{19/21}$-alkyl)-dimethylammonium methylsulfate An amount of 276.8 g (1 mol) of 1,2-epoxyalkane, with a portion of about 40% by weight $C_{16}$- and about 60% by weight $C_{18}$, were added at room temperature to 59.5 g (0.5 mol) of N-methyl diethanolamine, and then 1.5 g of 30% by weight methanolic sodium methylate solution were added. The reaction took place under stirring and nitrogen atmosphere after heating to 180° C. within 7 hours.

Subsequently 25.6 g of the first run were distilled off at a pressure of 0.4 mbar and a sump temperature of 240° C. Three hundred and fourteen grams (0.5 mol) of the reaction product bis(5-hydroxy-3-oxa-$C_{19/21}$-alkyl)-methylamine remained as a residue in the distillation flask. There was no further purification, and 63.1 g (0.5 mol) of dimethyl sulfate were added in drops to this reaction product under stirring at 70° C. to effect the quaternization, the stirring being continued for 2 hours at 70° C. The quaternized product was mixed with 75.4 g of isopropyl alcohol and 50.3 g of water. The 75% solution thus obtained was used for tests.

The reaction product of Example 1 no longer showed an epoxide band at 831 $cm^{-1}$ in the IR-spectrum before quaternization. It could be seen that the epoxy-alkane was completely reacted. Instead, the etherband appeared at 1120 $cm^{-1}$.

The maxima in the NMR spectrum which are characteristic of the structure, were at $\delta=4.3$; 3.6; 2.7; and 0.9 ppm. The integration ratio was 1:5:2:3. When heavy water was added, the maximum at $\delta=4.3$ ppm disappeared. This maximum could thus be associated with the hydroxyl group. The maxima at 1.3 and 0.9 ppm belong to the methylene or methyl group of the long alkyl ester.

The maximum at $\delta=3.6$ ppm belongs to the hydrogen atoms, which are linked with the carbon atoms adjacent to the oxygen atom. The maximum at $\delta=2.7$ ppm belongs to the hydrogen atoms which are linked with the carbon atoms adjacent to the nitrogen atom. Naturally, the signal of the hydrogen atoms of the methyl groups of the long alkyl radical appears as the most intensive maxima at 1.3 ppm.

Theoretically the unquaternized reaction product from Example 1 should show in the NMR spectrum maxima at $\delta=4$–5 ppm, as well as at $\delta=3.4$; 2.7; and 0.9 ppm, with an integration ratio of 1:5:2:3. The location of the maxima of the measured NMR-spectrum and the integration ratio are thus in good agreement with the theoretical values for this compound.

The NMR-spectrum of the reaction product of Example 2 shows prior to the quaternization, as expected, in addition to the other maxima which are also found in the spectrum of the product of Example 1, a maximum at $\delta=2.3$ ppm, which is characteristic of the N—$CH_3$ group. The measured integration ratio 2:10:4:3:6 is likewise in agreement with the theoretical integration ratio for this compound.

EXAMPLE 3

This example describes the use of a compound of Formula I according to the invention in the softening of washed fabrics. The product from Example 1 was tested for its softening action and the wetting behavior of fabrics treated with this product. The wetting behavior provided information on the absorbency of textiles, which plays an important role particularly in Turkish towels and in garments that come in contact with the skin.

The softening action was tested by moving a fabric of cotton or polyacrylic nitrile, which had been made hard by repeated washing, for 3 minutes at room temperature in an aqueous liquor (fabric to liquor ratio of 1:20), which contained 0.5% by weight active substance (based on the weight of the fabric); removing the aqueous liquor from the fabric is a centrifuge; and drying in air. The softness of the dried fabric was judged objectively by a group of people who had experience in this type of test.

The wettability was tested on cotton fabrics of 2×2 cm which had been treated as described above, by placing the samples on a water surface and measuring the time until the sample began to sink.

For comparison, a cationic commercial textile softener containing ditallowalkyl-dimethyl-ammonium chloride as an active substance, was used.

RESULTS

Cotton and polyacrylic nitrile textiles which had been treated with the product from Example 1 and with the comparison product, respectively, were found by the test persons to be soft. Only minor gradual differences were observed.

The following wettability values were measured:

TABLE 1

| Treatment | Wettability |
|---|---|
| Example 1 | 1 sec. |
| Ditallowalkyl-dimethylammonium chloride | > 300 sec. |
| Untreated | < 1 sec. |

These values show that the wettability of the fabrics treated with the compounds according to the invention is extremely good.

EXAMPLE 4

A softening preparation having the following composition was prepared:

5% by weight of bis(5-hydroxy-3-oxa-$C_{19/21}$-alkyl)-dimethylammonium chloride,
1% by weight of adduct from 1 mol of oleyl-cetyl alcohol +10 mols of ethylene oxide,
1% by weight of citric acid,
balance water

EXAMPLE 5

A softening preparation having the following composition was prepared:

20% by weight of bis(5-hydroxy-3-oxa-$C_{19/21}$-alkyl)-dimethylammonium chloride,
2% by weight of adduct from 1 mol of coconut alcohol ($C_{12}$–$C_{18}$)+4 mols of ethylene oxide,
1% by weight of glycolic acid,
20% by weight of isopropyl alcohol,
balance water

EXAMPLE 6

A softening preparation having the following composition was prepared:

6.0% by weight of bis(5-hydroxy-3-oxa-$C_{19/21}$-alkyl)-dimethylammonium chloride, 1.0% by weight of adduct from 1 mol of oleyl-cetyl alcohol +10 mols of ethylene oxide,
0.5% by weight of citric acid,
0.1% by weight of cotton brightener, 4,4-bis(2-anilino-4-morpholino-1,3,5-triazin-6-yl-amino)-stilbene-2,2'-disulfonic acid sodium salt,
1.0% by weight of benzyldodecyldimethylammonium chloride,
10.0% by weight of isopropyl alcohol,
balance water

EXAMPLES 7–14

Fully prepared, ready to use, after-treatment preparations of the following compositions (in percents by weight) were produced with the product of Example 1:

TABLE 2

| | Example | | | | | | | |
|---|---|---|---|---|---|---|---|---|
| Component | 7 | 8 | 9 | 10 | 11 | 12 | 13 | 14 |
| Tris(5-hydroxy-3-oxa-$C_{15/17}$-alkyl)-methylammonium chloride | 6.0 | 6.0 | 9.0 | 9.0 | 12.0 | 25.0 | 21.0 | 18.0 |
| Polyglycol ether (molecular weight 400) | 2.0 | 0.5 | 1.5 | 1.5 | 1.0 | — | — | — |
| N—$C_{12}$—$C_{18}$-acylaminopropyl)-N,N-dimethyl-N-carboxymethyl-aminobetaine | — | — | — | — | — | 5.0 | 4.0 | 0 |
| Lauryl trimethylammonium chloride | — | 1.0 | — | — | 1.5 | — | — | — |
| $C_{12/14}$-fatty alcohol ethoxylate with 3 mols ethylene oxide | — | — | — | 0.5 | 0.2 | — | — | — |
| Tallow fatty alcohol with 14 mols EO | — | — | — | — | — | — | — | 4.0 |
| $C_{12}$—$C_{18}$-fatty alcohol with 9 mols EO | — | — | — | — | — | 2.0 | 2.0 | — |
| Glycolic acid | 1.0 | 1.0 | — | — | — | — | — | — |
| Citric acid | — | — | 0.5 | 0.5 | 0.5 | — | — | — |
| Sodium-acetate | — | — | — | — | 0.1 | — | — | — |
| Optical brightener for polyamide | 0.1 | — | 0.1 | — | — | — | — | — |
| Isopropyl alcohol | 0.5 | — | 0.5 | 0.3 | — | — | — | 4.0 |
| 1,2-Propylene glycol | — | — | — | — | — | — | 4.0 | — |
| Perfume | 0.1 | 0.1 | 0.1 | 0.1 | 0.1 | 0.1 | — | 0.1 |
| Dye | — | 0.01 | — | 0.01 | — | 0.01 | — | — |
| balance water | | | | | | | | |

The laundry pieces treated with these products showed great absorbency and had a pleasant feel to the touch.

The following Examples 15 to 19 are directed to the use of a compound of Formula I according to the invention as a treating agent in the finishing of textiles. These examples show that soft, smooth textiles with improved hydrophilic and antistatic properties, as well as a reduced tendency to yellowing, are obtained according to the invention.

EXAMPLE 15

A swanskin fabric of pure cotton was treated in known manner with a liquor containing 20 g/l of a 20% by weight aqueous preparation of the compound produced according to Example 1 with a liquor absorption of 80% and then dried for 3 minutes at 110° C. The finished fabric had a full soft feel. In the determination of the absorption rate for water according to the height of rise method (DIN 53 924) in warp and weft direction, the following values were obtained:

TABLE 3

| Time | Warp | Weft |
|---|---|---|
| 30 | 30 | 30 |
| 60 | 45 | 45 |
| 180 | 60 | 65 |
| 300 | 70 | 70 |

The height of rise method measures the rate at which textile fabrics absorb water. The values indicated under warp and weft are in mm height of rise.

In comparison, a fabric finished according to the same method with a similar preparation having distearyldimethylammonium chloride as active substance, showed the following values:

TABLE 4

| Time (sec.) | Warp | Weft |
|---|---|---|
| 30 | — | — |
| 60 | — | — |
| 180 | 1 | 2 |
| 300 | 1 | 2 |
| 600 | 5 | 5 |

The fabric thus had no hydrophilic properties, while the feel corresponded substantially to that of the fabric finished according to the invention.

EXAMPLE 16

A fabric of cotton/polyester (63/35) was treated in known manner for 20 minutes at 40° C. with a liquor containing 0.6% by weight of the fabric weight of a preparation consisting of equal parts of the compound produced according to Example 1 and of a fatty acid polyaminamide from 1 mol $C_{14}$–$C_{18}$-fatty acid and 1 mol diethylene triamine (fabric to liquor ratio of 1:20). The fabric was subsequently dried at 110° C. The material obtained had a soft, full feel. The hydrophilic properties of the fabric according to the height of rise method (DIN 53 294) showed the following values:

TABLE 5

| Time (sec.) | Warp | Weft |
|---|---|---|
| 30 | 20 | 18 |
| 60 | 22 | 20 |
| 180 | 25 | 25 |
| 300 | 32 | 32 |

A skein finished for comparison with the same active substance of the fatty acid polyaminamide had a substantially identical feel but showed the following values:

TABLE 6

| Time (sec.) | Warp | Weft |
|---|---|---|
| 30 | — | — |

TABLE 6-continued

| Time (sec.) | Warp | Weft |
|---|---|---|
| 60 | — | — |
| 180 | — | — |
| 300 | 5 | 5 |

EXAMPLE 17

Viscose fibers were treated in known manner for 20 minutes at 45° C. in a liquor containing 0.5% of the fabric weight of a preparation from 8 parts of the compound produced according to Example 1, 10 parts of the fatty acid polyaminamide mentioned in Example 4, and 8 parts of a fatty alcohol polyglycol ether from 9 mols of a $C_{14}$–$C_{18}$-fatty alcohol and 5 mols ethylene oxide (fabric to liquor ratio of 1:10), and were subsequently dried. A fabric was obtained which had a pleasantly soft feel and was excellent to spin after addition of the conventional oiling materials. If water was applied by means of a pipette on a fleece formed of these fibers, it spread immediately and wet the fabric. However, on a fabric finished with the same amount of active substance distearyl-dimethylammonium chloride, water drops remained for more than 30 minutes.

EXAMPLE 18

A fabric of Diolen-loft (a polyester fabric available from Enka Glanzstoff AG) was treated in known manner with a liquor containing 3 g/l of a preparation of 14 parts of the compound produced according to Example 2 and 6 parts of the fatty alcohol polyglycol ether mentioned in Example 5, and was subsequently dried for 2 minutes at 110° C. The result was a soft fabric with an electric surface resistance of $2.0 \times 10^8$ ohm and a field decay-half life value of 0, measured in a normal climate.

When the same fabric was treated according to the same method with distearyldimethylammonium chloride, a fabric was obtained which had the same feel, but which had an electric resistance surface of $2.5 \times 10^9$ ohm and a field decay-half time value of 1.5 sec. This would lead to an electric charge in processing and in use.

EXAMPLE 19

A bleached and optically brightened shirt poplin of polyester/cotton (50/50) was treated in known manner in a liquor containing 4 g/l of the compound produced according to Example 2, and dried for 2 minutes at 110° C. When this fabric was subsequently exposed to a temperature of 120° C., it did not show yellowing.

When a fabric was treated for comparison with a condensation product from 1 mol of a $C_{16}$–$C_{18}$ fatty acid and 1 mol of a hydroxyl-polyethylene polyamine, it had the same hydrophilic properties but it showed a definite tendency to yellow.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A quaternary ammonium compound of formula

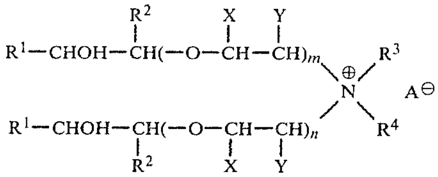

(I)

wherein $R^1$ represents an aliphatic hydrocarbon radical of from about 1 to 21 carbon atoms; $R^2$ represents hydrogen or has the same meaning as $R^1$, the total number of carbon atoms in $R^1$ and $R^2$ being from 6 to 22, and, when $R^2$ is hydrogen, $R^1$ has from 6 to 21 carbon atoms; $R^3$ represents an alkyl or hydroxyalkyl group having from 1 to 4 carbon atoms or a radical of formula

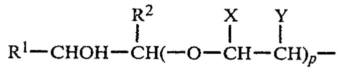

(Ia)

wherein $R^1$ and $R^2$ are as defined above, X and Y are each hydrogen or a methyl group, with the proviso that X and Y cannot be a methyl group, and p is an integer of from 1 to 20; $R^4$ represents an alkyl radical of from 1 to 4 carbon atoms; m and n are integers of from about 1 to 20; and $A^\ominus$ is an anion.

2. The compound of claim 1 wherein $R^3$ represents an alkyl or hydroxyalkyl group having from 1 to 4 carbon atoms.

3. The compound of claim 1 wherein $R^3$ represents a radical of formula

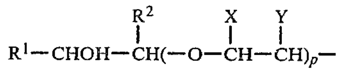

(Ia)

wherein $R^1$, $R^2$, X, Y, and p are as defined in claim 1.

4. The compound of claim 1 wherein $R^1$ represents an alkyl group of from about 1 to 21 carbon atoms.

5. The compound of claim 4 wherein $R^1$ represents an alkyl group of from about 8 to 18 carbon atoms.

6. The compound of claim 1 wherein $R^2$ is hydrogen.

7. The compound of claim 1 wherein X and Y are each hydrogen.

8. The compound of claim 1 wherein m, n, and p each represent a number of from 1 to 3.

9. The compound of claim 8 wherein m, n, and p are each 1.

10. The compound of claim 1 wherein $A^\ominus$ represents an anion selected from the group consisting of chloride, bromide, methyl sulfate, and ethyl sulfate.

11. The compound of claim 1 wherein $A^\ominus$ is a chloride or methyl sulfate anion.

12. The compound of claim 1 wherein $R^1$ represents an alkyl group of from about 8 to 18 carbon atoms; $R^2$, X, and Y each represent hydrogen; $R^3$ represents the radical $R^1$—CHOH—$CH_2$—O—$CH_2$—$CH_2$—;

$R^4$ represents a methyl group; m and n are each 1; and $A^\ominus$ represents a chloride or methyl sulfate anion.

13. The compound of claim 1 wherein $R^1$ represents an alkyl group of from about 8 to 18 carbon atoms; $R^2$, X, and Y each represent hydrogen; $R^3$ and $R^4$ each represent a methyl group; m and n are each 1; and $A^\ominus$ represents a chloride or methyl sulfate anion.

* * * * *

UNITED STATES PATENT AND TRADEMARK OFFICE

CERTIFICATE OF CORRECTION

PATENT NO. : 4,281,196

DATED : July 28, 1981

INVENTOR(S) : HORST RUTZEN ET AL.

It is certified that error appears in the above—identified patent and that said Letters Patent is hereby corrected as shown below:

Column 2, line 15: "N." should read -- No. --.

line 64: "21" should read -- 22 --.

line 64: Before "carbon" please insert

-- , and, when $R^2$ is hydrogen, $R^1$ has from 6 to 21 --.

Column 12, line 11: "is" should read -- in --.

Signed and Sealed this

*Thirteenth* Day of *October 1981*

[SEAL]

*Attest:*

GERALD J. MOSSINGHOFF

*Attesting Officer* *Commissioner of Patents and Trademarks*